United States Patent
Kute et al.

(10) Patent No.: US 7,601,117 B2
(45) Date of Patent: Oct. 13, 2009

(54) SYSTEMS AND METHODS FOR ASSISTING CARDIAC VALVE COAPTATION

(75) Inventors: Stephanie Kute, Piscataway, NJ (US); Steven Zung-Hong Wu, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 583 days.

(21) Appl. No.: 10/881,381

(22) Filed: Jun. 30, 2004

(65) Prior Publication Data

US 2006/0004247 A1   Jan. 5, 2006

(51) Int. Cl.
*A61N 1/362* (2006.01)

(52) U.S. Cl. .............................. 600/16; 600/17; 600/18; 600/37

(58) Field of Classification Search ............... 600/16, 600/17, 37, 151, 18; 606/151, 157; 604/51; 601/153

See application file for complete search history.

(56) References Cited

U.S. PATENT DOCUMENTS

| | | | |
|---|---|---|---|
| 5,037,379 A * | 8/1991 | Clayman et al. ............... 600/37 |
| 5,603,337 A * | 2/1997 | Jarvik ......................... 128/898 |
| 5,702,343 A * | 12/1997 | Alferness ..................... 600/37 |
| 5,759,187 A * | 6/1998 | Nakao et al. ................. 606/114 |
| 5,961,440 A * | 10/1999 | Schweich et al. ............. 600/16 |
| 6,076,013 A | 6/2000 | Brennan et al. |
| 6,077,214 A * | 6/2000 | Mortier et al. ................ 600/16 |
| 6,165,122 A * | 12/2000 | Alferness ..................... 600/37 |
| 6,193,648 B1 * | 2/2001 | Krueger ....................... 600/37 |
| 6,402,679 B1 * | 6/2002 | Mortier et al. ................ 600/16 |
| 6,402,680 B2 * | 6/2002 | Mortier et al. ................ 600/16 |
| 6,425,856 B1 * | 7/2002 | Shapland et al. .............. 600/37 |
| 6,595,912 B2 | 7/2003 | Lau et al. |
| 6,682,476 B2 | 1/2004 | Alferness et al. |
| 6,702,732 B1 | 3/2004 | Lau et al. |
| 6,723,038 B1 | 4/2004 | Schroeder et al. |
| 6,746,471 B2 | 6/2004 | Mortier et al. |
| 2001/0047122 A1 * | 11/2001 | Vanden Hoek et al. ........ 600/37 |
| 2002/0056461 A1 | 5/2002 | Jayaraman |
| 2002/0173694 A1 * | 11/2002 | Mortier et al. ................ 600/16 |
| 2003/0078465 A1 | 4/2003 | Pai et al. |
| 2004/0111101 A1 | 6/2004 | Chin |

OTHER PUBLICATIONS

M. M. Madani, M.D., "Mitral Valve Repair in the Treatment of Heart Failure", *Current Treatment Options in Cardiovascular Medicine*, vol. 6, pp. 305-311, (2004).

* cited by examiner

*Primary Examiner*—Carl H Layno
*Assistant Examiner*—Roland Dinga

(57) ABSTRACT

Systems and methods for reducing distention in designated portions of a heart muscle while assisting cardiac valve alignment and coaptation. Anchoring devices are secured to the heart muscle and a bio-compatible cardiac assist device placed over portions of the heart muscle is separately secured to the anchoring devices. The cardiac assist device may be a material that wraps portions of the heart muscle, or may be straps that wrap portions of the heart muscle. Tightening and securing the cardiac assist device in place helps to reduce distention in chambers of the heart muscle and aids alignment and coaptation of cardiac valves.

15 Claims, 8 Drawing Sheets

SYSTEMS AND METHODS FOR ASSISTING CARDIAC VALVE COAPTATION

BACKGROUND OF THE INVENTION

1. Field of the Invention

The invention generally relates to systems and methods for increasing cardiac output and efficiency. More specifically, the invention relates to systems and methods for reducing distention of one or more chambers of the heart and/or aligning one or more cardiac valves for better closure and coaptation thereof.

2. Related Art

Heart failure syndrome is a highly debilitating and degenerative disorder resulting from damage to the heart muscle. The damage to the heart muscle may be caused by a number of conditions, including coronary artery disease, long standing hypertension, leaky heart valve(s), and infections.

The disease of heart failure is common, lethal, and expensive to treat. An estimated 5.1 million Americans have heart failure with approximately 500,000 new cases diagnosed each year. In 1999, an estimated $20.3 billion in directs costs were spent for the care of heart failure patients. Heart failure is also the most common cause of hospitalization for patients 65 years and older in the United States. The mortality rate is 50% at five years for patients diagnosed with heart failure, and to date, there are limited treatment alternatives available.

Heart failure typically occurs when a weakened heart cannot pump an adequate amount of blood to meet the demands of the body's other organs and tissues. Malfunction of any of the valves within the heart can cause problems effecting the entire circulatory system. A leaky valve, for example, does not close properly and permits blood to flow backward as the heart contracts. As a result, the heart must contract and pump more often to compensate for the insufficient amount of blood supplied to the body by the normal cardiac pumping sequence. Overworking the heart in this manner damages the muscle of the heart and often masks underlying valvular disfunction.

Of the cardiac valves, the mitral valve is most often compromised as the powerful pumping action of the left ventricle tends to cause systolic outward bulging of an ischemic region of the left ventricle free wall. The ventricular wall pulls the entire associated muscle towards the left ventricle apex and laterally outwards. Misalignment of leaflets of the mitral valve and malfunction of the mitral valve thus often occurs. Though not as prevalent, the tri-cuspid valve is also susceptible to misalignment and malfunction due to the less aggressive pumping action of the right ventricle, which pumps blood to the lungs. In either case, coaptation of the leaflets of the cardiac valves is compromised, and cardiac output and efficiency is decreased.

Figure 1A:
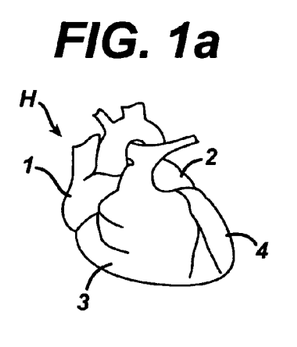
FIGS. 1a-c illustrates progressive states of deterioration of a heart representative of heart failure conditions.
Figure 1B:
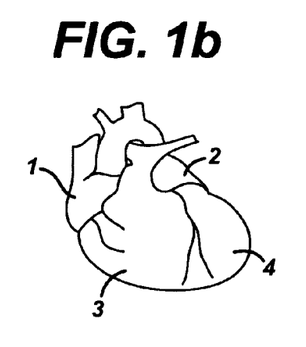
Figure 1C:
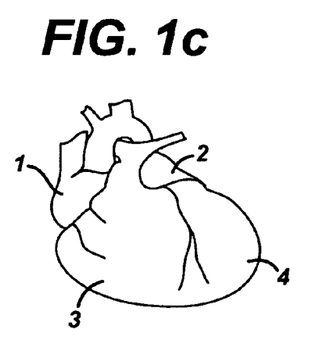

FIGS. 1a-1c show representative stages of progressive deterioration of a heart, wherein FIG. 1a shows a normal heart H with appropriately sized atrial chambers 1 and 2, and appropriately sized ventricular chambers 3 and 4. FIG. 1b shows slightly enlarged ventricular chambers 3 and 4, and FIG. 1c shows increasingly enlarged ventricular chambers 3 and 4. Ultimately, a complex process of damaging structural and functional changes to the heart results.

Normal cardiac valve closure depends upon the integrity of the myocardium, as well as the valve apparatus itself. The normal mitral valve, for example, is a complex structure comprising leaflets, an annulus, chordae tendineae, and papillary muscles. Any damage or impairment in function of any of these components can render the valve structure incompetent.

Surgical treatments of valvular dysfunction ranges from mitral ring annuloplasty to complete valve replacement using mechanical or tissue-based valve prosthesis. While being generally successful and routine in surgical practice today, these procedures are also costly, highly invasive and have high morbidity and mortality rates associated therewith. The paper "Mitral Valve Repair in the Treatment of Heart Failure" by Michael M. Madani, MD, published in Current Treatment Options in Cardiovascular Medicine 2004, 6:305-311, offers general information regarding valve repair techniques, and is hereby incorporated by reference in its entirety for all purposes.

Other device-based options for treating patients suffering from congestive heart failure include options for re-shaping, reinforcing and/or reducing the heart's anatomical structure. These options may use polymeric, metal, plastic, elastic or other bio-compatible materials providing external support to the heart muscle. Examples of such devices are evident in co-pending U.S. patent application Ser. Nos. 10/881,511 and 10/881,510 of common assignment herewith, the disclosures of which were filed on Jun. 30, 2004 and are incorporated by reference herein in their entirety. U.S. Pat. No. 6,425,856 similarly provides a cardiac constraint device comprised of a jacket made of biologicalty compatible material. Generally, such external support structures provide general relief to an otherwise compromised heart muscle and help to reduce the propensity of chambers of the heart to distend.

Figure 1D:
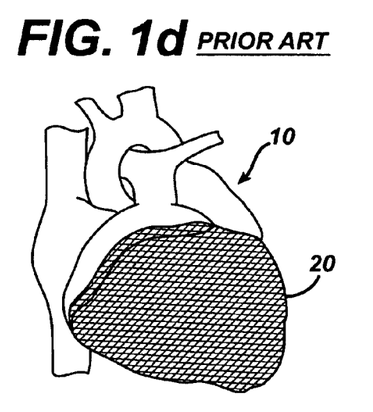
FIG. 1d illustrates a prior art mesh jacket placed around a heart.

FIG. 1d illustrates an example of a cardiac assist device of the prior art in the form of a jacket 20 providing external support to the heart H. The jacket 20 surrounds a valvular annulus of the heart and at least the ventricular lower extremities of the heart. Once positioned as desired around the heart, the jacket 20 is sutured to the heart. The jacket 20 thus works on a passive, mechanical level to reduce periodic myocardial over-stretch and wall stress, and serves as a constant "reminder" to the heart of how the heart should perform. The jacket, however, does not address localized valve mis-alignment and coaptation concerns that often occur due to myocardial over-stretch and wall stress. Moreover, suturing the jacket 20 around a circumference of the heart is a time-consuming and cumbersome procedure. Further still, precise positioning and securing of the jacket about the heart using endoscopic tools and techniques as the heart is beating has proved challenging.

In view of the above, a need exists for systems and methods that increase cardiac output and efficiency by reducing distention of one or more cardiac chambers while aligning one or more cardiac valves for better coaptation and function thereof.

SUMMARY OF THE INVENTION

The systems and methods of the invention provide a cardiac assist device positioned and secured around portions of a heart to reduce distention of one or more chambers of the heart while aiding alignment and coaptation of one or more cardiac valves. The systems and methods of the invention further provide anchoring devices separately secured to the heart, wherein the cardiac assist device is secured to one or more of the anchoring devices.

In some embodiments of the systems and methods of the invention, the cardiac assist device, for example, is a strap that wraps around a circumference of a designated portion of the heart whereat distention is to be reduced. Once in the desired position about the heart, ends of the strap are pulled to tighten the strap. The tightened strap is then secured to one or more of the anchoring devices to maintain the strap in the desired position. Tightening and securing the strap in this manner supports the heart at a specified location that helps to reduce the propensity of that portion of the heart to distend. At the same time, the tightened and secured strap aids the alignment and coaptation of one or more of the cardiac valves of the heart due to the localized position of the strap around the heart. In various embodiments of the systems and methods of the invention, the ends of the strap are secured to one another in addition to being secured to one or more of the anchoring devices. The artisan should appreciate that additional straps may be used in similar manner to reduce distention of other portions of the heart and to further aid alignment and coaptation of one or more of the cardiac valves.

In other embodiments of the systems and methods of the invention, the cardiac assist device is comprised of a biocompatible material as disclosed in co-pending U.S. patent application Ser. Nos. 10/881,511 and 10/881,510 (referenced above. For example, the material of the cardiac assist device may comprise an open first end with a seam about its periphery and a second end opposite the first end as disclosed in co-pending U.S. patent application Ser. No. 10/881,511 referenced above. The second end may be closed to form a sack-like cardiac assist device, or open to form a tubular-like cardiac device. In either case, the heart is received in the material of the device until an apex of the heart approaches the second end of the cardiac assist device and the seam at the first end of the material is positioned around the circumference of that portion of the heart whereat distention is to be reduced. The seam is then tightened and secured to one or more of the anchoring devices already secured to the heart. The tightening and securing of the seam in this manner reduces distention of that portion of the heart and aids the alignment and coaptation of one or more of the cardiac valves in that localized area of the heart. Increased cardiac efficiency and output may be achieved as a result.

In other embodiments of the systems and methods of the invention, the seam may instead comprise a drawstring. The drawstring may be incorporated into the material of the cardiac assist device, for example, as in co-pending U.S. patent application Ser. No. 10/832,942 referenced above. The drawstring is tightened and secured to one or more of the anchoring devices to aid the alignment and coaptation of one or more of the cardiac valves of the heart due to the localized position of the drawstring around the heart. In this manner, distention is decreased and better coaptation of the intended one or more cardiac valves tends to be achieved In various embodiments of the systems and methods of the invention, the anchoring devices, for example, are as disclosed in U.S. patent application Ser. Nos. 10/881,511 and 10/881,510, both of which have been incorporated herein by reference in their entirety. The anchoring devices are each separately secured to the heart, and the cardiac assist device is secured to the anchoring devices.

According to the systems and methods of the invention, a plurality of ports, or other openings, are provided through a chest wall of a patient or subject. The ports, or other openings, may simply be an opening within the chest wall or below the chest wall of the patient (subxyphoid). In either case, the opening may be held open with tape or some other retraction device. The ports, or other openings, provide access to a chest cavity of the patient or subject. The anchoring devices, conventional instruments for manipulating and securing the anchoring devices to the heart, and visualization means are inserted into the chest cavity of the patient or subject through the plurality of ports, or openings. The cardiac assist device is also inserted into the chest cavity of the patient or subject through one of the ports, or openings.

The anchoring devices are separately secured to the heart using the instruments and visualization means inserted through the plurality of ports, or openings, in the chest wall of the patient or subject. Thereafter, the cardiac assist device is manipulated to a desired position about portions of the heart. The cardiac assist device is then tightened and secured to one or more of the anchoring devices in order to maintain the cardiac assist device in the specified location about the heart. By tightening and securing the cardiac assist device at a localized portion of the heart, distention of that portion of the heart may be reduced and alignment of a targeted one or more of the cardiac valves in that portion of the heart may be achieved. Increased cardiac output and efficiency tends to occur as a result.

Ideally, the same instruments used to place and secure the anchoring devices to the heart are also used to place, fit and secure the cardiac assist device to the anchoring devices. The visualization means may be an endoscope, a fiber-optic cable, or a camera on an elongate member for example, permitting a medical professional to view the various procedures performed as they occur according to the invention.

The various embodiments of the system and methods of the invention described herein provide several advantages over prior known devices and methods of applying a cardiac assist device to a heart. The various embodiments of the system and methods according to the invention minimize the time and cumbersome efforts previously required to fit and suture a cardiac assist device around an entire circumference of the heart. The various embodiments of the systems and methods according to the invention target a localized area of the heart to reduce the propensity of the heart to distend in that area. As a result, the systems and methods of the invention simultaneously aids alignment and coaptation of cardiac valves when the cardiac assist device is tightened and secured to one or more of the anchoring devices that are separately secured to the heart. Increased cardiac output and efficiency is rendered more likely as a result. Further, the various embodiments of the systems and methods of the invention may be performed endoscopically, even during beating heart procedures, which renders a precise fit of the cardiac assist device and optimal alignment of the intended cardiac valves more likely.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Figure 2:
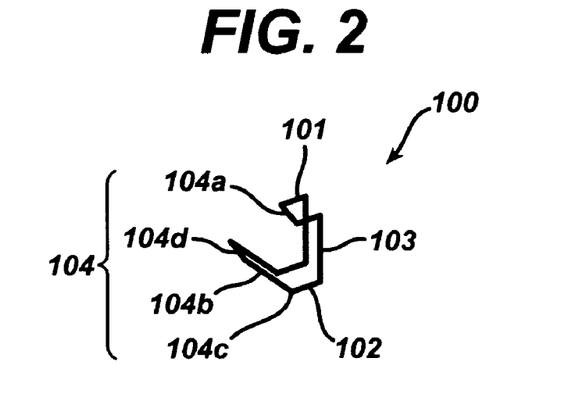
FIG. 2 illustrates an anchoring device according to the invention.
Figure 3:
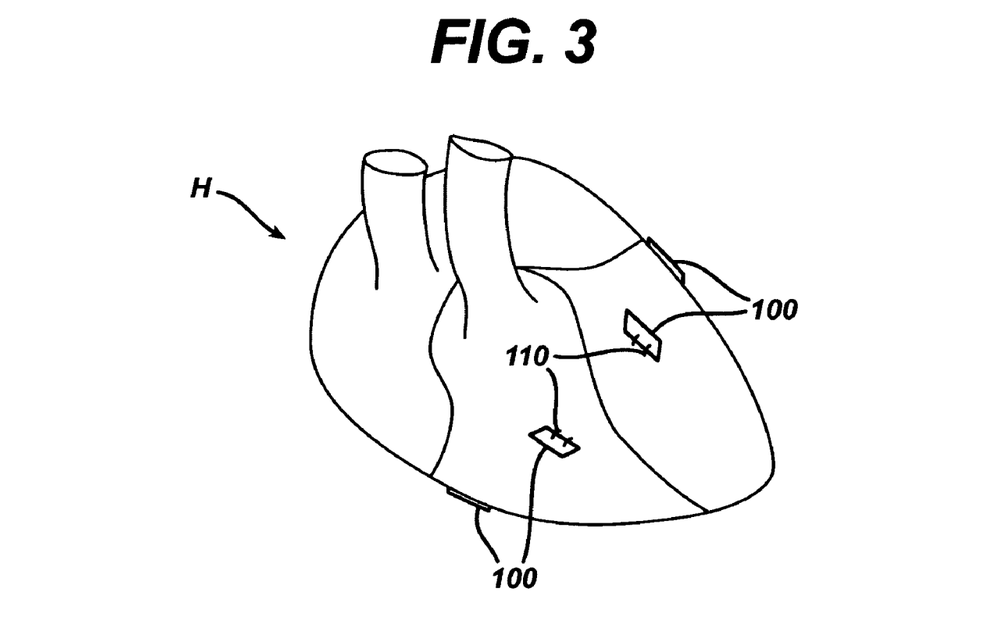
FIG. 3 illustrates the anchoring device of FIG. 2 secured to various location on a heart according to the invention.
Figure 4:
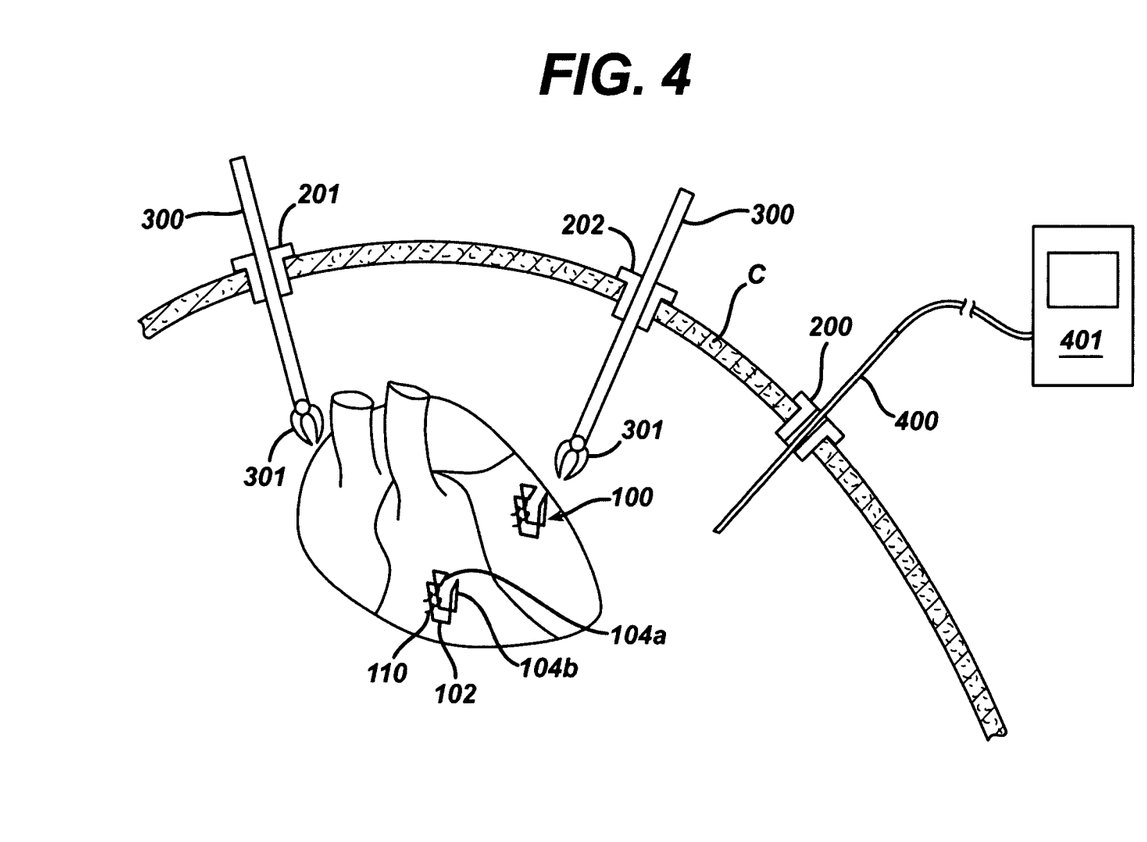
FIG. 4 illustrates various openings through a chest wall of a patient or subject and various instruments inserted therethrough for placing and securing the anchoring devices to the heart according to the invention.

FIGs. 2-4 illustrate anchoring devices 100 according to the systems and methods of the invention. The anchoring devices 100 are placed on and secured to the heart at designated locations. The anchoring devices may be secured to the heart using sutures 110 u-clips, staples, or other securing means known in the art. The anchoring devices are similar to those anchoring devices disclosed in U.S. patent applications Ser. Nos. 10/881,511 and 10/881,510referenced above.

As shown most clearly in FIG. 2, each anchoring device 100 is a frame-like member comprised of a top 101, a bottom 102, a back 103, and a front 104. The front 104 is further comprised of a lip 104a, and pivotable flange 104b. The pivotable flange 104b has a hinged end 104c attached to the bottom 102 of the anchoring device, and a free end 104d opposite the hinged end. The pivotable flange 104b engages the lip 104a, when the pivotable flange 104b is rotated about the hinged end 104c, to close the front of the anchoring device 100. Of course the artisan will appreciate that the anchoring device could as well be comprised of a first member pivotable with respect to a second member that is secured to the heart, pivotable encompassing material deflection between two sections of a unitary device as well as two members joined in a pivotable manner. Accordingly, the first and second members engage one another to close and capture a part of the cardiac assist device thereby securing the wrap to the anchoring devices, similar to that shown in FIG. 2. Though captured, the cardiac assist device is constrained in generally two directions, but remains free to move laterally with respect to the anchoring device 100. Alternately, the cardiac assist device may be fixed to the anchoring device 100.

Alternately, the anchoring device may be a single piece design capable of flexing onto itself to capture a cardiac assist device. For example, a shape memory material such as a nitinol, or another material exhibiting similar properties, may be formed to transition itself into a closed position to capture a cardiac assist device. A restraint may be provided to prevent the transition until desired by the medical professional performing the cardiac assist procedure. In yet another embodiment, the anchoring device may be a barb or an eyelet, through and/or around which some portion of a cardiac assist device could be passed and/or secured. Other variations may become apparent to those skilled in the art in light of the instant disclosure without departing from the scope of the present invention.

FIG. 3 illustrates generally as many as six anchoring devices 100 placed on and secured to the surface of the heart H. The artisan should appreciate, however, that as few as one anchoring device could provide a means of securing a cardiac assist device thereto. Of course, it should be further appreciated that more than six anchoring devices may also be used. FIG. 3, for example, illustrates two anchoring devices 100 on the posterior side of the heart, two anchoring devices 100 on the anterior side of the heart, and one anchoring device on each lateral side of the heart. Sutures 110, u-clips, staples or other securing means known in the art are used to secure the anchoring devices to the heart.

In practice, as shown in FIG. 4, for endoscopic procedures utilizing the systems and method of the invention a plurality of ports 200, 201, 202, or other openings, are provided through the chest wall C of a patient or subject. The ports 200, 201, 202, or openings, are provided in conventional manner and may be, for example, trocar tubes. The anchoring devices 100 are placed into a chest cavity of the patient or subject through one or more of the ports 200, 201, 202, or openings. The anchoring devices 100 are then maneuvered and placed onto the surface of the heart using a grasper 300, or other conventional instrument, also inserted through one or more of the ports 200, 201, 202. Each instrument 300 has grasping elements 301 at a distal end thereof, whereas proximal ends of each instrument 300 extend externally from the chest cavity for manipulation by a medical professional. A visualizing means, such as an endoscope 400, fiber optic cable, or camera on an elongate member, for example, is placed into the chest cavity of the patient or subject through one of the ports 200, 201 202, or openings, as well. The endoscope, for example, may include a monitor 401 external to the patient or subject to provide the medical professional with views of the interior chest cavity as the procedures according to the invention occur therewithin. Of course the artisan will appreciate that the systems and method of the invention may be used in practice non-endoscopically, ie via open-chest procedures as well.

The artisan should appreciate that the use of fewer instruments in the chest cavity provides a less cluttered working environment and easier maneuverability of the instruments involved in the procedures occurring in the chest cavity according to the invention. A visualizing means, such as an endoscope 401, is inserted through one of the ports 200, 201, 202, or openings, to permit the medical professional to view the procedures as they occur. When the anchoring devices are placed on a posterior side of the heart, a conventional suction instrument (not shown) may be additionally inserted through one of the ports 200, 201, 202 in order to lift the heart slightly while the placement and securing of the anchoring devices on the posterior side of the heart occurs. Alternatively, a fork-like instrument (not shown) as is known in the art, could be used to lift or stabilize the heart as well.

Referring still to FIG. 4, once placed at designated locations on the surface of the heart, each anchoring device 100 is secured to the heart using conventional securing means such as sutures 110, u-clips, staples, adhesives or other securing means known in the art. Endoscopic suturing instruments, for example, as are known in the art, may be inserted through one of the ports 200, 201, 202, or openings, to secure the anchoring devices to the heart.

Figure 5:
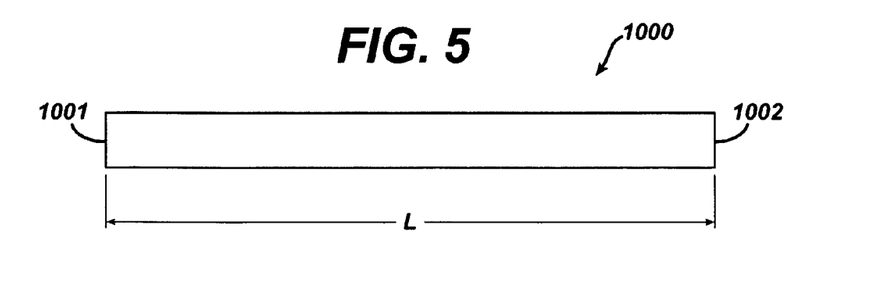
FIG. 5 illustrates an embodiment of a cardiac assist device according to the invention.

FIG. 5 illustrates an embodiment of a cardiac assist device according to the systems and methods of the invention. As shown in FIG. 5, the cardiac assist device includes a strap 1000 comprised of a first end 1001 and a second end 1002, the second end being opposite the first end. The strap has a length L that is sufficient to wrap around a circumference of the heart at a designated portion of the heart. The strap 1000 is further comprised of a bio-compatible material such as MERSELENE®, PROLENE®, stainless steel, c-flex, or other material known in the art that is suitable for providing support to designated portions of the heart while remaining on the heart within the chest cavity of a patient or subject. Preferably, the strap 1000 has an expanded width, as shown, to distribute the force applied to the heart muscle. This reduced the incidence of abrasion against the heart tissue. Alternately or additionally, a coating may be applied to the strap 1000 to reduce friction and thereby reduce abrasion, or a pad may be placed between the strap 1000 and the heart tissue.

Figure 6:
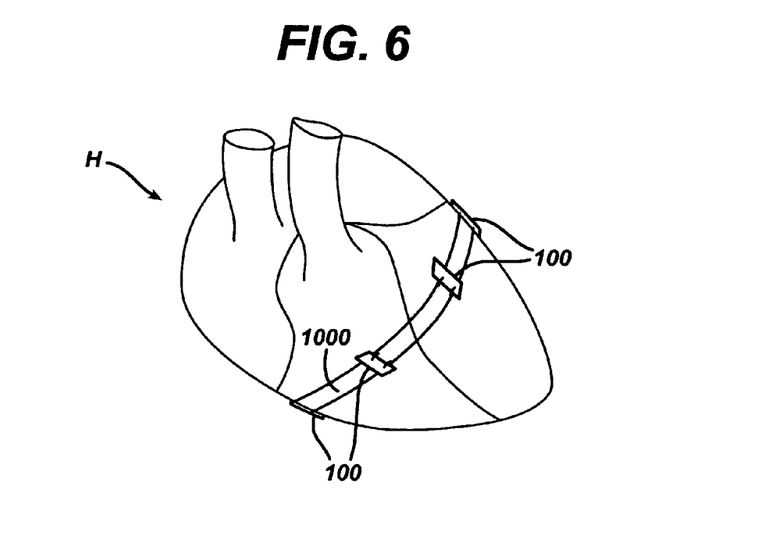
FIG. 6 illustrates the cardiac assist device of FIG. 5 received in anchoring devices and wrapped around the heart.

FIG. 6 illustrates the cardiac assist device of FIG. 5 positioned within anchoring devices 100 and wrapped around the heart. When wrapped around the designated portion of the heart, the strap 1000 is secured to the anchoring devices previously secured to the heart at the designated portions of the heart.

Figure 7A:
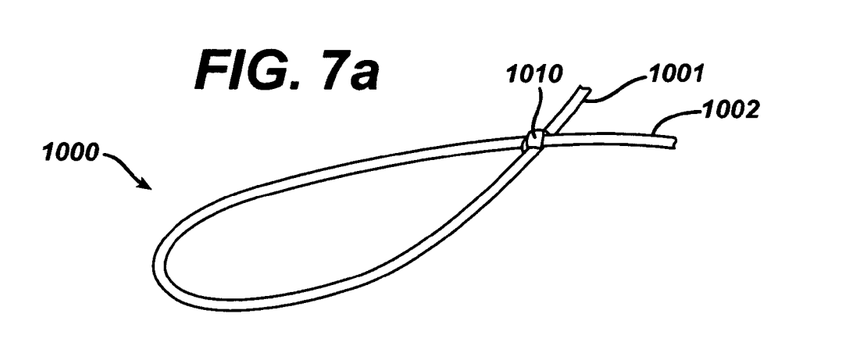
FIGS. 7a-7e illustrate various embodiments of the cardiac assist device of FIG. 5.
Figure 7B:
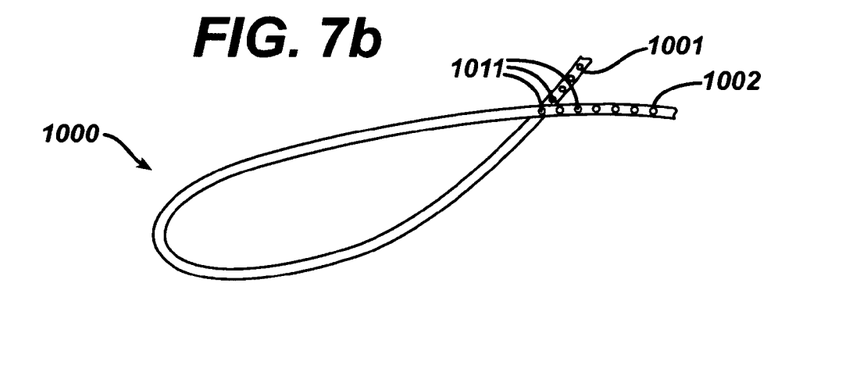
Figure 7C:
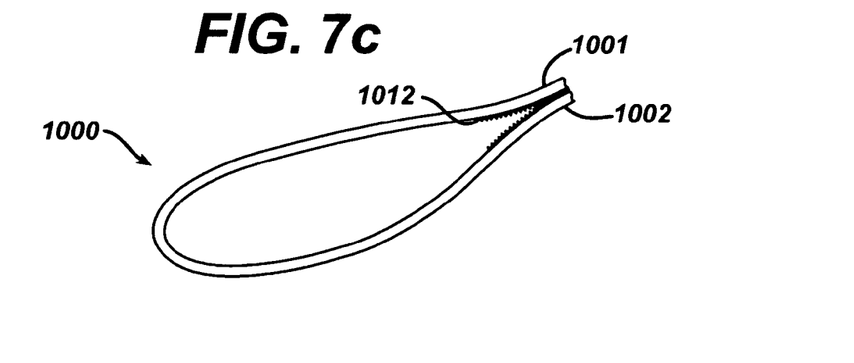
Figure 7D:
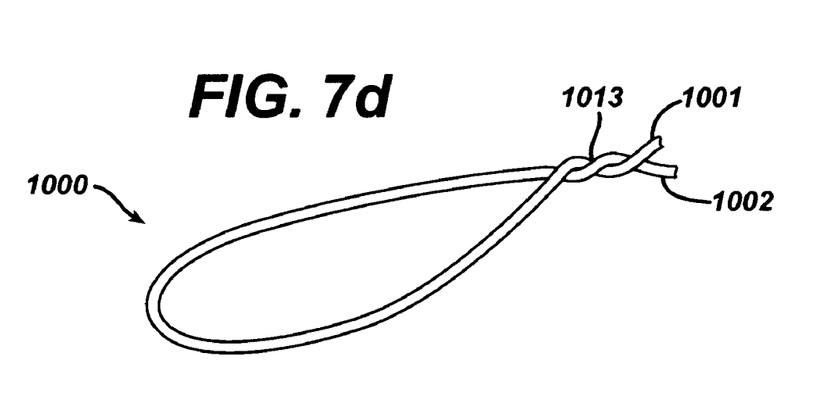
Figure 7E:
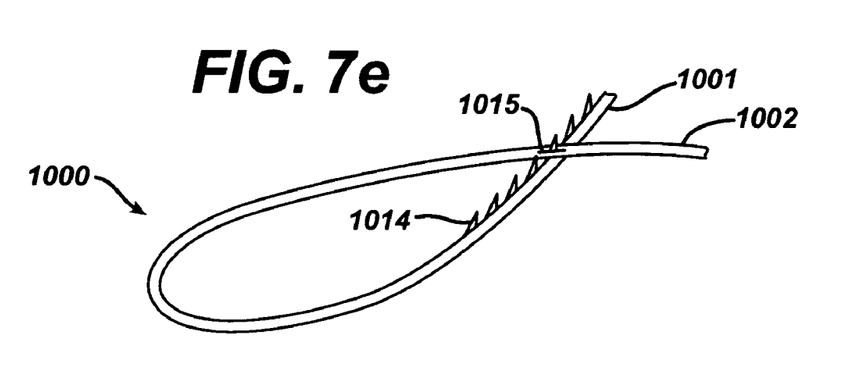

As shown in FIGS. 7a-7e, various other embodiments of the strap 1000 secure the first end 1001 and the second end 1002 of the strap together. FIG. 7a secures the first end 1001 to the second end 1002 of the strap by tying the ends into a knot 1010. FIG. 7b, for example, secures the first end 1001 to the second end 1002 of the strap by snapping buttons 1011 together. FIG. 7c, for example, secures the first end 1001 to the second end 1002 of the strap by zipping teeth 1012 together. FIG. 7d secures the first end 1001 to the second end 1002 of the strap by twisting the spirals 1013 of the ends together. FIG. 7e, for example, secures the first end 1001 to the second end 1002 of the strap by cable-tying notches 1014 with receiving member 1015. Of course, the artisan should appreciate that the first and second ends may be secured to one another using other securing means known in the art. Graspers, for example, as are known in the art, may be inserted through one of the openings to secure the first end 1001 and the second end 1002 of the strap 1000 together according to the various embodiments of the strap described above.

Figure 8A:
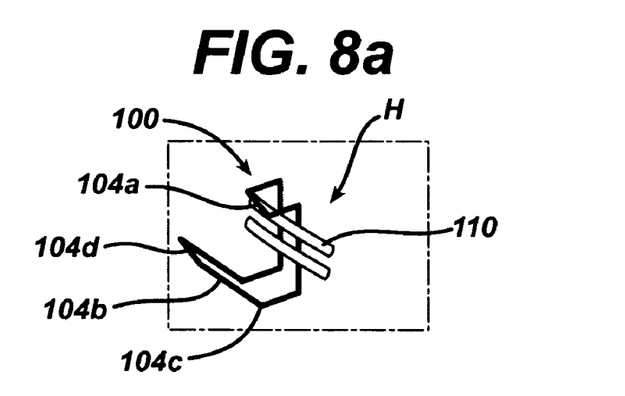
FIGS. 8a-8c illustrate various stages of an anchoring device receiving the cardiac assist device of FIG. 5 according to the invention.
Figure 8B:
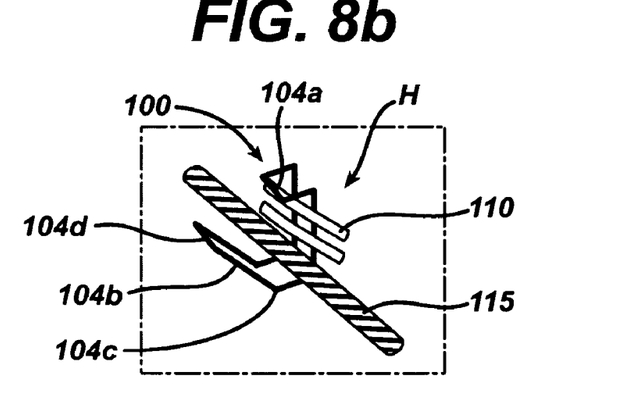
Figure 8C:
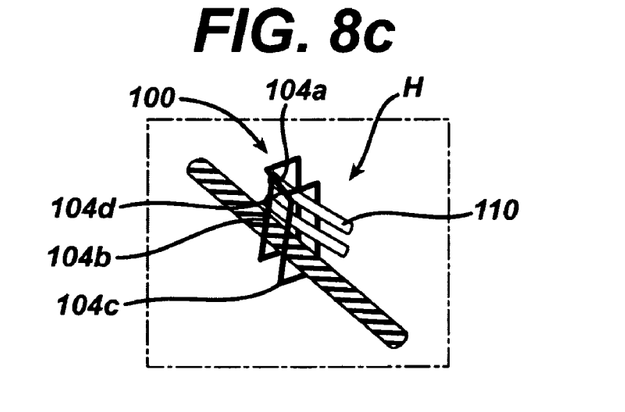

In practice, referring now to FIGS. 8a-8c and FIG. 4, for endoscopic procedures utilizing the systems and method s of the invention wherein the chest wall, various ports, instruments and visualizing means are omitted from illustration in FIGS. 8a-8c but understood to exist as in FIG. 4, one of the anchoring devices 100 is shown secured to the heart H by sutures 110, for example. In FIG. 8a, the pivotable flange 104b is in an open position, i.e., not engaging the lip 104a. In FIG. 8b, the strap 1000 as the cardiac assist device of FIG. 5, for example, is positioned within the opened anchoring device 100 provided inserted into the chest cavity through one of the ports, or openings, 200-202. One of the instruments 300, for example, is used to position the strap 1000 within the opened anchoring devices as described above. The flange 104b of the anchoring device is then manipulated, using the same instruments 300, for example, to engage the lip 104a and close the anchoring device, as shown in FIG. 8c. In this manner, the strap 1000 is maintained within anchoring device at the intended localized region of the heart where distention is sought to be reduced and where better valvular alignment and coaptation is sought to be achieved.

Referring still to FIGS. 8a-8c and FIG. 4, the first end 1001 and the second end 1002 of the strap 1000 are then pulled and tightened by instruments 300. Once tightened, the strap is secured to the anchoring device 100, or to itself. In either case, the strap 1000 is captured within the anchoring device 100. The strap 1000 may be secured to the anchoring device 100 by sutures, using conventional endoscopic suturing instruments, for example, or by other securing means known in the art. The strap 1000 may also be secured to itself in accordance with any of the various embodiments of the strap 1000 shown in FIGS. 7a-7e, for example, or by other securing means known in the art. Ideally the same instruments and visualizing means used to place and secure the anchoring devices (FIG. 4) are used to place and secure each strap 1000 within the appropriately located anchoring devices 100.

The anchoring devices 100 are strategically placed around the heart to reduce distention and to aid valvular alignment and coaptation at targeted areas of the heart when the cardiac assist device is positioned therein. For example, to reduce left ventricular distention and to aid alignment of the mitral valve between the left atrium and left ventricle, anchoring devices are placed and secured to the heart along the cardiac midline near the left atrium and left ventricle junction (FIG. 6). Of course, the artisan should appreciate that additional anchoring devices, and correspondingly additional straps, may be placed superior or inferior to the cardiac midline region to reduce distention of designated portions of the heart and to further aid alignment of one or more cardiac valves.

Because each strap is adjustable, more normal or ideal cardiac function may be promoted by the appropriate placement and adjustment of each strap. A transesophageal echocardiograph, for example, could be used simultaneously with strap adjustment to establish when improved cardiac function has been achieved. For example, where a patient is undergoing a fibrillating or bypass procedure, each strap may be initially placed loosely within the anchoring devices, and the heart may be monitored using the transesophageal echocardiograph. After normal or ideal cardiac function has resumed, each strap may then be adjusted and secured to the anchoring devices, or to itself, to support the designated portions of the heart.

Experimentation by the inventors has shown that placing and securing anchoring devices on the heart near the cardiac midline region at the left atrium and left ventricle junction, and separately securing cardiac assist devices to the anchoring devices has reduced localized distention of the heart and has simultaneously increased cardiac output and efficiency by providing better alignment and coaptation of the mitral valve. For example, where initial left ventricular pressure was 70.8 mmHg without the cardiac assist device in place, the left ventricular pressure increased to 80.2 mmHg after the cardiac assist device was in place, tightened and secured to the anchoring devices as described herein.

Because relatively few surgical instruments are required to place, tighten and secure the cardiac assist device to the heart, the medical professional is better able to fit the cardiac assist device to the heart. At the same time, the medical professional is able to view the procedures of placing and securing the cardiac assist device to the heart resulting in easier and more precise sizing of the cardiac assist device to the heart even as the heart beats. As a result, smaller ventricular volume and a more pointed apex of the heart is more likely to be achieved due to the systems and methods herein described.

Figure 9A:
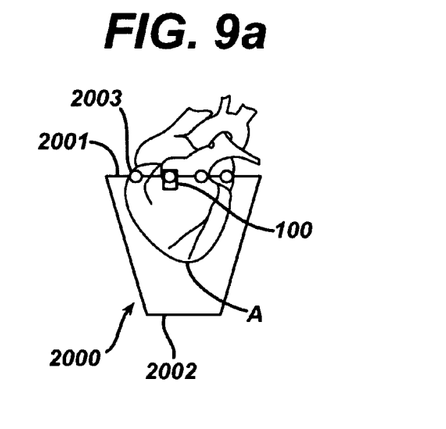
FIGS. 9a-9b illustrate other embodiments of a cardiac assist device according to the invention.
Figure 9B:
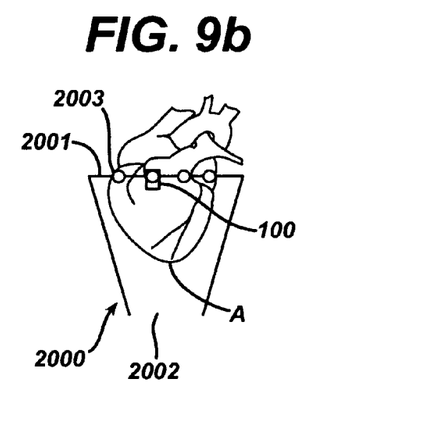

FIGs. 9a and 9b illustrate other embodiments of a cardiac assist device 2000 according to the systems and methods of the invention. As shown in Figs. 9a and 9b, the cardiac assist device is comprised of bio-compatible material having an open first end 2001 and a second end 2002 opposite the first end as disclosed in U.S. patent application Ser. No. 10/811, 511 referenced above. The first end includes a seam 2003 along a periphery of the material. The second end 2002 may be closed (Fig. 9a) to form a sack-like cardiac assist device, or the second end may be open (Fig. 9b) to form a tubular-like cardiac assist device. In either case, the material comprising the cardiac assist device may be a polymeric, a metal, a plastic, an elastic, or other material known in the art suitable for surrounding the heart and reducing the propensity of chambers of the heart to distend.

In practice, anchoring devices are placed into the chest cavity through ports and secured to the heart using conventional grasping instruments 300 and securing means as before with reference to FIG. 4. The cardiac assist device 2000 is then inserted endoscopically, for example, into the chest cavity through one of ports 200, 201, 202. The instruments 300 position the cardiac assist device as desired about the heart, and insert the seam 2003 of the cardiac assist device 2000 into the opened anchoring devices. The instruments 300 are then manipulated further by the medical professional to close the anchoring devices and to tighten the seam. Once tightened, the seam is secured to the anchoring devices 100. Sutures, clips, staples or other securing means known in the art may be used to secure the seam to the anchoring devices. As before, a visualizing means, such as an endoscope, is inserted through one of the ports to permit the medical professional to observe the procedures as they occur. Tightening and securing the seam in this manner reduces distention at that portion of the heart whereat the seam is located and aids alignment and coaptation of one or more cardiac valves as well. Of course, as before the procedures could instead be performed non-endoscopically, via open-chest procedures, in the discretion of the medical professional.

Figure 10:
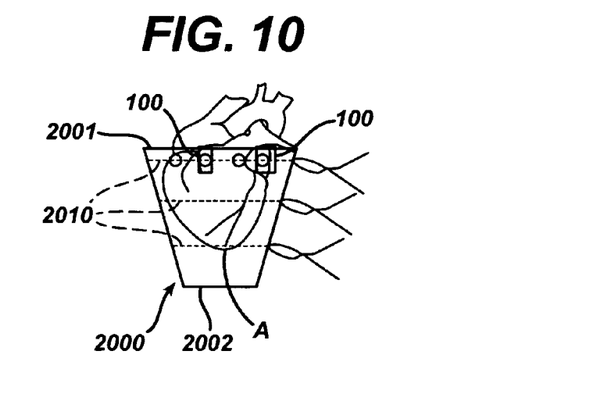
FIG. 10 illustrates another cardiac assist device according to the invention.

FIG. 10 illustrates yet another embodiment of the cardiac assist device according to the system and methods of the invention. The cardiac assist device of FIG. 10 is generally the same as that of FIG. 9a except that the cardiac assist device 2000 of FIG. 10 further comprises at least one drawstring 2010 (three drawstrings shown). Each drawstring 2010 is incorporated into the material of the cardiac assist device as disclosed in U.S. patent application Ser. No. 10/881,511 referenced above. A drawstring 2010 at the first end 2001 of the cardiac assist device 2000 of FIG. 10 generally replaces the seam 2003 of the cardiac assist device 2000 of FIG. 8a.

In practice, where endoscopic procedures are used, the cardiac assist device 2000 of FIG. 10 is positioned about the heart generally as discussed above with reference to the cardiac assist device 2000 of FIG. 9a and 9b. Once positioned as desired about the heart, the instruments 300 are manipulated by the medical professional to tighten and secure each drawstring to the anchoring devices 100 or to itself. At least one drawstring 2010 and/or seam 2001 would be captured within an anchoring device 100. the drawstrings may be secured using known securing means such as tying clipping, twisting, cable-tying, zipping, for example, as disclosed in U.S. patent application Ser. No. 10/881,511 referenced above. As before, tightening and securing the drawstrings in this manner reduces distention at that portion of the heart whereat one of the drawstrings is located and may additionally aid alignment and coaptation of one or more cardiac valves as well. Increased cardiac output and efficiency tends to occur as a result. Of course, the cardiac assist device 2000 may be inserted, placed and secured using non-endoscopic procedures as well.

The artisan should appreciate, with respect to the embodiments of the systems and methods of the invention shown in FIGS. 9a-10, that the material of the cardiac assist device may be further fitted to the heart using an appropriate material gathering means, such as a reduction ring or additional drawstrings, as disclosed in U.S. patent application Nos. 10/881,511 and 10/881,510 referenced above.

The procedures and apparatus according to the present invention are considerably less invasive and quicker than alternative valve repair procedures. A patient who suffers from both cardiac distention and valve malfunction can be treated by the present inventive methods, and achieve improved valve function as well, obviating the need for more invasive valve repair. Further, as described above, the efficacy of the treatment can be monitored and/or adjusted in real time. Additionally, the cardiac assist device could relatively easily be adjusted in a minimally invasive subsequent procedure, for example to address subsequent degeneration of the heart muscle.

The various exemplary embodiments of the invention as described hereinabove do not limit different embodiments of the present invention. The bio-compatible material, described herein is not limited to the materials, designs, or shapes referenced herein for illustrative purposes only, and may comprise various other materials, designs or shapes suitable for the procedures described herein as should be appreciated by one of ordinary skill in the art.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. An apparatus for reinforcing a heart, the apparatus comprising:
    at least one anchoring device adapted to be secured to the heart; and
    a cardiac assist device captured by the anchoring device and adapted to surround designated portions of the heart to aid alignment and coaptation of one or more valves of the heart,
    wherein the anchoring device comprises a first member adapted to be securable to the heart and a second member pivotably joined with the first member, thereby allowing capture of the cardiac assist device.

2. The apparatus according to claim 1, wherein the cardiac assist device comprises a bio-compatible material.

3. The apparatus according to claim 1, wherein the cardiac assist device further comprises an open first end opposite a closed second end, and a seam about a periphery of the first end, an apex of the heart approaching the second end of the material when the heart is received within the material.

4. The apparatus according to claim 3, wherein the seam is captured by the anchoring device, tightened and secured thereto to fit the cardiac assist device to the designated portions of the heart.

5. The apparatus according to claim 4, further comprising sutures to secure the seam in position.

6. The apparatus according to claim 1, wherein the cardiac assist device comprises at least one strap, the strap surrounding designated portions of the heart.

7. The apparatus according to claim 6, wherein the strap further comprises opposed ends having securing means to secure the strap surrounding the designated portions of the heart.

8. The apparatus according to claim 7, wherein the securing means is selected from a group consisting of sutures, zippers, snaps, clips, tie-knots, cable-ties, and twists.

9. The apparatus according to claim 1, wherein the cardiac assist device further comprises an open first end opposite an open second end, the first end having a peripheral seam, wherein an apex of the heart approaches the second end when the heart is received within the material.

10. The apparatus according to claim 9, wherein the seam is captured by the anchoring devices, tightened and secured thereto to fit the material to the designated portions of the heart.

11. The apparatus according to claim 9, further comprising sutures to secure the seam in place.

12. The apparatus according to claim 1, wherein the cardiac assist device further comprises an open first end, a second end opposite the first end, and at least one drawstring operative to vary the size of the cardiac assist device.

13. The apparatus according to claim 12, wherein the at least one drawstring is captured by one or more anchoring device, and tightened to fit the material to the designated portion of the heart.

14. The apparatus according to claim 12, further comprising two or more drawstrings operative to vary the size of the cardiac assist device, each drawstring located at different portions of the heart.

15. The apparatus of claim 1, wherein the first member comprises a frame-like structure having a top, a bottom and a back connecting the top and the bottom and securable to the heart, and the second member comprises a front pivotably joined with one of the top and bottom of the first member and pivotably engageable with the other of the top and the bottom of the first member.

* * * * *

UNITED STATES PATENT AND TRADEMARK OFFICE
CERTIFICATE OF CORRECTION

| | | |
|---|---|---|
| PATENT NO. | : 7,601,117 B2 | Page 1 of 1 |
| APPLICATION NO. | : 10/881381 | |
| DATED | : October 13, 2009 | |
| INVENTOR(S) | : Kute et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1050 days.

Signed and Sealed this

Fifth Day of October, 2010

David J. Kappos
*Director of the United States Patent and Trademark Office*